US005789387A

United States Patent [19]

Hector et al.

[11] Patent Number: 5,789,387
[45] Date of Patent: Aug. 4, 1998

[54] METHODS AND COMPOSITIONS FOR TREATING FUNGAL INFECTIONS IN MAMMALS

[75] Inventors: Richard Fredrich Hector; Akram Sabouni, both of Moss Beach, Calif.

[73] Assignee: Shaman Pharmaceitucals, Inc., South San Francisco, Calif.

[21] Appl. No.: 697,706

[22] Filed: Aug. 27, 1996

Related U.S. Application Data

[63] Continuation-in-part of Ser. No. 520,289, Aug. 28, 1995.
[51] Int. Cl.$^6$ .................................................. A61K 31/70
[52] U.S. Cl. .................. 514/43; 514/50; 536/28.53; 536/28.54; 536/28.55; 536/28.8; 424/568
[58] Field of Search .................. 514/43, 50; 536/28.53, 536/28.54, 28.55, 28.8; 424/468

[56] References Cited

U.S. PATENT DOCUMENTS

| | | | |
|---|---|---|---|
| 4,315,922 | 2/1982 | Hagenmaier et al. | 514/43 |
| 4,552,954 | 11/1985 | Moeschler et al. | 536/28.53 |
| 4,851,389 | 7/1989 | Hector | 514/43 |
| 4,914,087 | 4/1990 | Hector et al. | 514/50 |
| 5,006,513 | 4/1991 | Hector et al. | 514/43 |
| 5,019,560 | 5/1991 | Hector et al. | 514/43 |
| 5,091,375 | 2/1992 | Hector et al. | 514/50 |
| 5,096,889 | 3/1992 | Hector et al. | 514/43 |
| 5,134,126 | 7/1992 | Hector et al. | 514/43 |
| 5,149,795 | 9/1992 | Hector et al. | 536/28.8 |
| 5,194,427 | 3/1993 | Hector et al. | 514/43 |
| 5,229,123 | 7/1993 | Masubichi et al. | 424/408 |
| 5,236,900 | 8/1993 | Cooper et al. | 514/19 |
| 5,238,926 | 8/1993 | Cooper et al. | 514/50 |
| 5,326,561 | 7/1994 | Harman et al. | 424/94.61 |
| 5,330,976 | 7/1994 | Hector et al. | 514/43 |
| 5,389,609 | 2/1995 | Woloshuk et al. | 514/12 |
| 5,433,947 | 7/1995 | Harman et al. | 424/94.61 |
| 5,461,055 | 10/1995 | Cooper et al. | 514/269 |

OTHER PUBLICATIONS

Krainer et al., "Chemochromatography: Its Use for the Separation of Nikkomycins X and Z," *Analytical Biochem.*, 160(1), 233–239 (Jan. 1987).

Hector et al. (X), "Synergistic Action of Nikkomycins X and Z with Papulacandin B on Whole Cells and Regenerating Protoplasts of *Candida albican*", *Antmicrobial Agents & Chemotherapy*, 29(3), 389–394 (Mar. 1986).

Valdivieso et al., "*CAL 1*, A Gene Required for Activity of Chitin Synthease 3 in *Saccharomyces cerevisiae*", *J. Cell Biology*, 114(1), 101–109 (Jul. 1991).

Shaw et al., "The Function of Chitin Synthase 2 and 3 in the *Saccharomyces cerevisiae* Cell cycle," *J. Cell Biology*, 114(1), 111–123 (Jul. 1991).

Yadan et al., "Sensitivity to Nikkomycin Z in *Candida albicans:* Role of Peptide Permeases," *J. Bacteriology*, 160(3), 84–888 (Dec. 1984).

Hector et al. (XI), "Inhibition of Chitin Synthesis in the Cell Wall of *Caccidioides im mitis* by Polyoxin D," *J. Bacteriology*, 154(1), 488–498 (Apr. 1983).

Barnes et al., 1983, "Host–Parasite Interactions in the Pathogenesis of Experimental Renal Candidiasis", Lab. Invest. 49:460–467 (Issue No. 4).

Becker et al., 1983, "Polyoxin D Inhibits Growth of Zoopathogenic Fungi", Antimicrob. Agents chemother. 23:926–929 (Issue #6, Jun. 1983).

Becker et al., 1988, "Use of the Chitin–Synthesis Inhibitor Nikkomycin to Treat Disseminated Candidiasis in Mice", J. Infect. Dis. 157-212-214(Jan. 1988).

Cabib, 1991, "Differential Inhibition of Chitin Synthetases 1 and 2 from*Saccharomyces cerevisiae* by Polyoxin D and Nikkomycins", Antimicrob. Agents chemother. 35:170–173 (Iss.No. 1, Jan. 1991).

Cassone, 1989, "Cell Wall of *Candida albicans:* Its Functions and Its Impact on the Host", Curr. Top. Med. Mycol. 3:248–314.

Chapman et al., 1993, Abstracts of the Conference on Candida and Candidiasis: Biology, Pathogenesis, and Management, Abstract No. A/20.

Chapman et al., "Chitin Biosynthesis in *Candida albicans* Grown In Vitro and In Vivo and Its Inhibition by Nikkomycin Z", Antimicrob. Agents Chemother. 36:1909–1914(Iss.No. 9, Sep. 1992).

Hector, "Compounds Active against Cell Walls of Medically Important Fungi", Clinical Microbiol. Reviews 6:1–21 (Jan. 1993, Issue No. 1).

Hector and Schaller, 1992, "Positive Interaction of Nikkomycins and Azoles against *Candida albicans* in vitro and In Vivo", Antimicrob. Agents Chermother. 36:1284–1289)Iss.No. 6, Jun. 1992).

Hector et al., Apr. 1990, "Evaluation of Nikkomycin X and Z in Murine Models of Coccidioidomycosis, Histoplasmosis, and Blastomyosis", Antimicrob. Agents and Chermother. 34:587–593(Iss.No. 4).

Isono et al., 1965, "studies on Polyoxins, Antifungal Antibiotics: Part I. Isolation and Characterization of Polyoxins A and B", Agr. Biol. and Chem. 29:848–854 (Issue No. 9).

Longer and Robinson, Chapter 91 in *Remingtton's Pharmaceutical Sciences*, Gennaro, A.R., ed., Mack Publishing Company, Easton, PA, 1990, Chapter 9, pp. 1676–1693.

Louria, 1977, "Experimental Infections with Fungi and Yeasts", Contrib. Microbiol. Immuno. 3:31–47.

Naider et al., 1983, "Synthesis and Biological Activity of Tripeptidyl Polyoxins as Antifungal Agents", Antimicrob. Agents Chemther. 24:787–796 (Issue No. 5, Nov. 1983).

*Primary Examiner*—John Kight
*Assistant Examiner*—L. Eric Crane
*Attorney, Agent, or Firm*—Pennie & Edmonds LLP

[57] ABSTRACT

Methods of treating fungal infections are disclosed. The methods comprise administering a chitin synthesis inhibitor to a mammal in a continuous fashion so that at least a minimum effective concentration is maintained in the mammal's plasma or in a target organ. In a preferred embodiment, the administration is by continuous intravenous infusion and the fungal infection is due to *Candida albicans*. In another preferred embodiment, the administration is by a sustained release formulation and the fungal infection is due to *Candida albicans*.

25 Claims, 6 Drawing Sheets

METHODS AND COMPOSITIONS FOR TREATING FUNGAL INFECTIONS IN MAMMALS

This is a continuation-in-part of U.S. patent application Ser. No. 08/520,289 filed Aug. 28, 1995, the entire disclosure of which is incorporated herein by reference.

1. FIELD OF THE INVENTION

The present invention relates generally to a method of using compounds capable of inhibiting chitin synthesis to treat infections due to fungi in mammals. In a particular embodiment, the present invention is directed to the use of a class of compounds known as nikkomycins to treat infections of *Candida spp.* in mammals.

2. BACKGROUND OF THE INVENTION

2.1. FUNGAL INFECTIONS

Fungal infections are a common and often serious health problem. In particular, systemic candidiasis is one of the major causes of morbidity and mortality in immunocompromised individuals, particularly those patients who are neutropenic, suffering from acquired immune deficiency syndrome (AIDs), or who are undergoing immunosuppression for transplantation or therapy for cancer. *Candida albicans* is one of the most common fungi causing disease in such patients. Although many sites of infection are possible in these individuals, and systemic infection is often observed, the kidney is the target organ in many cases (Louria, D. B., 1977, Contrib. Microbiol. Immunol. 3:31).

There is an extensive literature on animal models of candidiasis, and rodent renal models are perhaps the most widely used and accepted versions of those models. In these models, infection is initiated with an intravenous challenge of the yeast and a progressive infection establishes itself in the kidney. Invariably, death results from renal insufficiency. Experimental therapies with antifungal drugs administered by various routes are well documented, and are considered predictive of the human response to these same therapies.

2.2. INHIBITORS OF CHITIN SYNTHESIS

Drugs that are currently available to combat fungal infections have significant limitations, chief among these being nephrotoxicity. In view of these limitations, it would be of great value to have new classes of antifungal drugs or to develop new methods of using already known drugs. Since the cell walls of fungi are structures that have an important role in pathogenesis (Cassone, A., 1989, Curr. Top. Med. Mycol. 3:248-314), and the components of fungal cell walls are not found in the cells of mammals, one possibility for the development of such new drugs or methods would be to investigate compounds that affect the synthesis of fungal cell walls.

Chitin is an important component of most fungal cell walls. Compounds inhibitory to the synthesis of chitin have been reported to have demonstrable effects against medically important fungi, particularly against dimorphic fungi that are highly chitinous (U.S. Pat. No. 4,851,389), as well as fungi of agricultural importance (U.S. Pat. No. 4,315,922 and U.S. Pat. No. 4,552,954). The compounds mentioned in the cited patents, nikkomycins, together with similar agents known as polyoxins, are known to act by interfering with the synthesis of chitin in the cell walls of fungi (Cabib, E., 1991, Antimicrob. Agents Chemother. 35:170-173). Because of the varying content of chitin in different fungi, plus the different role of chitin in the cell walls of different fungi, differences in susceptibility to the nikkomycins have been described for various fungi both in vitro and in vivo (Hector and Pappagianis, J. Bacteriol., 1983, 154:488-498; Hector et al., Antimicrob. Agents Chemother., 1990, 34:587-593; Hector and Schaller, Antimicrob. Agents Chemother., 1992, 36:1284-1289; Hector, R. F. Clinical Microbiol. Reviews, 1993, 6:1-21; Becker et al., J. Infect. Dis., 1988, 157:212-214; Naider et al, Antimicrob. Agents Chemother., 1983, 24:787-796; Becker et al., Antimicrob. Agents Chemother., 1983, 23:926-929; Chapman et al., Antimicrob. Agents Chemother., 1992, 36:1909-1914).

*Candida albicans* was found to be relatively resistant to chitin synthesis inhibitors, requiring millimolar concentrations and prolonged periods of incubation to kill this yeast (Naider et al, Antimicrob. Agents Chemother., 1983, 24:787-796; Becker et al., Antimicrob. Agents Chemother., 1983, 23:926-929). In contrast, highly chitinous dimorphic fungi, such as *Coccidioides immitis*, were found to be rapidly susceptible to both polyoxin D and nikkomycin Z at concentrations ranging from 60-100 micromolar (Hector and Pappagianis, J. Bacteriol., 1983, 154:488-498; Hector et al., Antimicrob. Agents Chemother., 1990, 34:587-593). The relative resistance of *C. albicans* to this class of compounds is likely due to the less important role of chitin in the cell wall of *C. albicans*, plus the compensatory mechanisms that the yeast invokes when confronted with the agent (Hector, Clin. Microbiol. Rev., 1993, 6:1-21).

Becker et al., Antimicrob. Agents Chemother., 1983, 23:926-929 found that upon prolonged periods of exposure to polyoxin D, Candida cells exhibited a phenomenon called "chaining". Although deformed, these cells were able to survive several replications, though ultimately they became sensitive to osmotic pressures and would lyse. Subsequently, *C. albicans* was found to be more sensitive in vitro to nikkomycins than polyoxins, but treatment with nikkomycin nevertheless resulted in cells that were able to survive the treatment by creating the same morphologic forms as were observed after treatment with polyoxin (Yadan et al., J. Bacteriol., 1984, 160:884-888).

Becker et al., J. Infect. Dis., 1988, 157:212-214 (Becker et al.) reported the first in vivo studies of mice infected with this yeast and treated with nikkomycin Z. Although Becker et al. were able to demonstrate a delay in the onset of mortalities in infected mice treated with bolus intravenous injections of nikkomycin Z given once daily for periods up to 20 days, essentially all mice died shortly after cessation of therapy. Becker et al. did not disclose the continuous intravenous administration of nikkomycin Z or any other method of continuous administration. The results of Becker et al. were characterized by others in the art as showing only "modest efficacy" (Hector and Schaller, Antimicrob. Agents Chemother., 1992, 36:1284-1289, at page 1284) and "limited efficacy" (Chapman et al., Antimicrob. Agents Chemother., 1992, 36:1909-1914, at page 1913).

In other survival experiments, animals were treated orally with nikkomycin Z over a 10-14 day period (Hector and Schaller, Antimicrob. Agents Chemother., 1992, 36:1284-1289) (Hector and Schaller). Hector and Schaller obtained similar findings in that animals ultimately succumbed to infection. In yet other experiments, mice infected intravenously with *C. albicans* were treated subcutaneously with high concentrations of nikkomycin Z and the kidneys of the infected mice were cultured for the quantitative recovery of yeasts. Although the amount of nikkomycin Z used was shown to depress chitin synthesis in vivo, the authors reported "poor efficacy" in that the treatment did not result in any reduction in numbers of yeasts (Chapman et al., Antimicrob. Agents Chemother., 1992, 36:1909-1914).

Chapman et al., 1993, Abstracts of the Conference on Candida and Candidiasis: Biology, Pathogenesis, and Management. Abstract No. A/20 (Chapman abstract) were able to demonstrate some protection by nikkomycin Z against experimental candidiasis in a mouse model when the nikkomycin was given by subcutaneous injections. However, the timing of the injections, which began only one hour after the inoculation of the yeast into the experimental animals (i.e., before the infection had time to become established), suggests that this study was not a good model for natural Candida infections and thus has limited value as a predictor of therapeutic success for the method of administration of nikkomycin described therein.

This is especially true if one considers the several reports that describe the histopathology of renal infection due to Candida as being a phenomenon which occurs over a prolonged time period. For example, Barnes et al., 1983, Lab. Invest. 49:460-467 (Barnes) describes the course of infection as follows:

At 5 minutes following injection [with *C. albicans*] blastospores were observed to be localized predominantly within glomerular and peritubular capillaries of the cortex.

At 2 hours, localization of *C. albicans* remained primarily within the glomerular and peritubular capillaries of the cortex; however, most yeast were associated with one or several polymorphonuclear leukocytes (PMNs). Frequently, yeasts with short germ tubes were observed within PMNs.

Lesions at 6 hours were characterized by the presence of small inflammatory nodules within glomerular and peritubular capillaries. Rarely, germ tubes were observed penetrating the inflammatory nodule and adjacent capillaries and tubules.

At 10 hours, inflammatory nodules within capillaries were larger than at 6 hours and usually contained yeasts. Penetration of inflammatory nodules, capillaries, and tubular epithelium by germ tubes or maturing mycelia was a frequent observation and usually occurred without injury to host cells.

It is important to realize that in the experiment described in the Chapman abstract (in which all three doses of nikkomycin Z were given within 9 hours of infection) the drug could easily reach the yeast because they were still likely confined to the capillaries (and hence the circulation). The yeast do not start to invade the tissues in significant numbers until the 10 hour interval, as described by Barnes. Thus, the approach of the Chapman abstract does not constitute therapeutic intervention in the traditional sense because access to the target organism by the drug would be markedly different after the 10 hour interval, just as it would be in a normal clinical setting. Because of the free access of the drug to the yeast, the approach taken by the Chapman abstract has made the mouse a "fur lined test tube" and is more analogous to an in vitro test than to a therapeutic in vivo assessment of the antifungal properties of nikkomycin Z.

In all of the studies described above in which nikkomycin Z was administered in a therapeutically realistic manner, i.e., with a reasonable delay between the challenge with yeast and the administration of the nikkomycin, the nikkomycin appeared to be acting at best in a fungistatic fashion with only marginal activity in promoting survival and only limited ability to reduce the fungal burden in the kidneys.

3. SUMMARY OF THE INVENTION

The present inventors have found that continuously administered inhibitors of chitin synthesis are markedly effective in preventing morbidity and mortality in animals suffering from fungal infections. In particular, nikkomycin Z has been demonstrated to be effective in such animals. In marked contrast to previous reports of use of nikkomycin Z, the duration of therapy is short, the dose used is low, yet the results are superior to those of the prior art.

According to the methods of the present invention, nikkomycins have been found effective in treating a mammal having an infection due to *Candida spp*. Such fungi include *C. albicans* and related species. In one embodiment, the nikkomycin is nikkomycin Z administered in a continuous fashion in an amount sufficient to treat infection of the yeast in a mammal. In another embodiment, the amount of nikkomycin is sufficient to inhibit the enzyme chitin synthase for a period of time sufficient to result in the death of the fungi. According to the present invention, continuous treatment with nikkomycin is particularly useful against systemic Candida infections in humans. Additionally, continuous treatment with nikkomycin is useful against more localized Candida infections in humans.

The present invention also encompasses sustained release formulations of chitin synthesis inhibitors, including but not limited to a nikkomycin such as nikkomycin Z.

5. DETAILED DESCRIPTION OF THE INVENTION

The present invention provides methods of preventing morbidity and mortality in mammals due to fungal infections by the continuous administration of chitin synthesis inhibitors. In particular, the continuous administration of nikkomycin Z has been found to be especially effective in combatting infections due to *Candida albicans*. Although the prior art taught that nikkomycins were of limited effectiveness against *Candida spp.*, the present inventors have surprisingly found that when administered in a continuous fashion, nikkomycin Z is highly effective.

By continuous administration is meant administration in which a more or less constant amount of nikkomycin or other chitin synthesis inhibitor is delivered per unit time to the subject mammal and in which a more or less steady state concentration of the nikkomycin or other chitin synthesis inhibitor is achieved in the plasma or in a target organ of the subject mammal. This is to be contrasted with discontinuous methods of administration in which the nikkomycin or other chitin sythesis inhibitor is delivered either once or repeatedly, with large amounts of time separating each repeated delivery. It is believed that continuous administration results in the achievement of prolonged and consistently high levels of nikkomycin or other chitin synthesis inhibitors in the plasma or target organs of the subject mammal. In contrast, discontinuous administration is believed to result in the achievement of an initial high level of nikkomycin or other chitin synthesis inhibitor followed by a fall in levels until the next delivery again results in a high level.

In one embodiment of the present invention, the nikkomycin is administered in a continuous fashion in an amount sufficient to treat infection of the fungus in a mammal. In another embodiment, the amount of nikkomycin is sufficient to inhibit the enzyme chitin synthase for a period of time sufficient to result in the death of the fungi.

As used herein, therapeutically effective means able to result in clinical improvement in the signs and symptoms of disease and/or prevention of mortality in the more critically ill. Therapeutically effective amount or concentration means an amount or concentration sufficient to result in clinical improvement in the signs and symptoms of disease and/or prevention of mortality in the more critically ill. Minimum effective concentration (MEC) means the minimum concentration of a chitin inhibitor in plasma or a target organ (e.g., kidney) that is therapeutically effective.

The subject of the methods of the present invention is a mammal, including but not limited to mammals such as cows, pigs, horses, cats, dogs, etc., and is preferably a human. In the case of human subjects, the subject may be an immunocompromised subject such as one who suffers from acquired immune deficiency syndrome (AIDS), is neutropenic, or is undergoing immunosuppression for transplantation or therapy for cancer.

The methods of the present invention are particularly suitable for the treatment of infections due to *Candida spp.* Such *Candida spp.* include, but are not limited to: *Candida albicans, Candida parapsilosis, Candida krusei, Candida tropicalis, Candida glabrata.*

In addition to nikkomycins, other chitin synthesis inhibitors will be suitable for use in the methods of the present invention. Examples of such chitin syntesis inhibitors are polyoxins, such as polyoxin D.

5.1. ROUTES OF ADMINISTRATION AND SUSTAINED RELEASE COMPOSITIONS

The inhibitors of chitin synthesis employed in the methods of the present invention may be administered by any method such that at least a minimum effective concentration (MEC) of inhibitor is maintained in the plasma or in a preselected organ of the subject mammal for a time sufficient to be therapeutically effective.

In a preferred embodiment, the method of administration is by continuous intravenous delivery. Such continuous intravenous delivery is to be contrasted with discontinuous methods of delivery such as: the bolus intravenous injections of nikkomycin Z given once daily in Becker et al., J. Infect. Dis., 1988, 157:212-214; the oral administration of Hector and Schaller, Antimicrob. Agents Chemother., 1992, 36:1284-1289; and the subcutaneous injections of Chapman et al., 1993, Abstracts of the Conference on Candida and Candidiasis: Biology, Pathogenesis, and Management. Abstract No. A/20. It is believed that continuous intravenous delivery permits the buildup and maintenance of a therapeutically effective concentration of chitin inhibitor in the plasma or affected organs of the subject mammal.

In addition to continuous intravenous administration, other routes of continuous administration are useful in the present invention. For example, well known sustained release methods that permit sustained release of chitin synthesis inhibitors by the per-oral, intramuscular, or subcutaneous routes are effective as long as the sustained release method is effective in building up an MEC in the subject mammal for a time sufficient to be therapeutically effective. Sustained release methods include diffusion systems in which the rate of release of a chitin synthesis inhibitor is determined by its diffusion through a water-insoluble polymer. The inhibitor can be present as a core surrounded by the polymer, as in reservoir devices; alternatively, the inhibitor can be dispersed in a matrix of polymer. Other sustained release methods include the use of implants for subcutaneous tissues and various body cavities as well as the use of transdermal devices. For a discussion of sustained release methods see Longer, M. A. and Robinson, J. R., Chapter 91 in *Remington's Pharmaceutical Sciences*, Gennaro, A. R., ed., Mack Publishing Company, Easton, Pa., 1990.

A successful sustained release formulation requires the right combination of: (1) a fast enough release (short lag time) to provide the loading dose; (2) a slow enough release (long mean residence time (MRT)) to prolong the maintenance of the plasma concentration of the chitin synthesis inhibitor above the MEC; and (3) a nikkomycin or other chitin synthesis inhibitor depot adequate to achieve steady state nikkomycin or other chitin synthesis inhibitor concentrations above the MEC in the infected tissues for a prolonged time. Generally, the time necessary will be about 1–5 days, preferably 3–4 days.

For the per-oral route of administration, the nikkomycin or other chitin synthesis inhibitor can be incorporated into microspheres which could erode over time, slowly releasing the nikkomycin or other chitin synthesis inhibitor into the gastrointestinal tract. The materials employed to make the matrix of the microspheres can vary. These materials include, but are not limited to, polylactic acid/polyglycolic acid copolymers, starch, gelatin, gum arabic, agar, agarose, stearic acid, polyethylene glycols, waxes such as beeswax, and the like. The desired release profile can be achieved by adjusting the amount of nikkomycin or other chitin synthesis inhibitor loaded into the microspheres. The microspheres could also be pressed into a tablet or filled into a capsule to facilitate per-oral delivery.

Another per-oral delivery system incorporates nikkomycin or another chitin synthesis inhibitor into an osmotic pump, which can be designed to attain the desired drug release rate.

For the intramuscular and subcutaneous route of administration, the nikkomycin or other chitin synthesis inhibitor is dissolved in (or incorporated into) a semi-solid dosage form such as an emulsion or ointment Additionally, the nikkomycin or other chitin synthesis inhibitor can be incorporated into microspheres which then are suspended in a semi-solid formulation to achieve the desired release pattern. Examples of suitable carriers for semi-solid dosage forms for the present invention include, but are not limited to: Gelucire® (a mixture of glycerol and polyethylene fatty acid esters), the glycol ethers and derivatives such as polyethylene glycol(s), polypropylene glycol, "MYVEROL®" 18-92 (propylene glycol monoesters), cholesterol, vegetable oil, and "PLURONIC®" F127 (copolymers of ethylene oxide and propylene oxide). These materials and other suitable carriers can be employed individually or in a combination of two or more. The release rate of the nikkomycin or other chitin synthesis inhibitor from the semi-solid formulation can vary depending upon the composition of the semi-solid as well as the ratio of the nikkomycin or other chitin synthesis inhibitor to the semi-solid. All the above sustained release formulations are encompassed in the present invention.

The following semi-solid sustained release formulations are among those suitable for use in the present invention.

Formula A: the formulation contains 12% lecithin, 5% ethyl alcohol, 5% dimethylsulfoxide (DMSO), 10% corn starch, and 68% saline. Lecithin is suspended into a mixture of ethyl alcohol and DMSO using 5 minutes sonication followed by 5 minutes of vortexing. Corn starch is then added along with saline and the mixture is vortexed, heated to 40° C., and sonicated for 5 minutes. The vortexing, heating, and sonicating steps are repeated two more times until a homogeneous semi-solid phase is obtained.

Formula B: the formulation contains 3% lanolin, 14% cottonseed oil, 6% "TWEEN®" 40 (polyoxyethylenesorbitan monopalmitate), 4% stearic acid, 2% hydroxymethylcellulose, 1% carbopol, and 70% saline. Stearic acid and lanolin are suspended into cottonseed oil and heated to 70° C. while stirring for a period of 5 minutes. A second solution of carbopol and hydroxymethylcellulose in saline is prepared using stirring, heating, and sonication. Both vehicles are homogenized together using "TWEEN®" 40 (polyoxyethylenesorbitan monopalmitate) as the emulsifying agent. The mixture is heated to 40° C. and mixed using a stirrer for a period of 1 hour.

Formula C: the formulation contains 2% polyethylene glycol hydroxy stearate (Solutol, BASF Corporation, Parsippany, N.J.), 2% petrolatum white, 2% "TWEEN®" 20 (polyoxyethylenesorbitan monolaurate), 4% sorbitan monopalmitate (Span 40 Sigma Chemical Co., St. Louis, Mo.), 2.5% mineral oil, 3.5% polyoxyethylene sorbitan monostearate ("TWEEN®" 60 [polyoxyethylenesorbitan monostearate]), 2% carbopol, 2% beeswax, 1% xanthan gum, and 79% saline. White petrolatum and beeswax are heated to 60° C. and mixed with Solutol (BASF Corporation, Parsippany, N.J.), Span 40 (Sigma Chemical Co., St. Louis, Mo.), and "TWEEN®" 20 (polyoxyethylenesorbitan monolaurate) to constitute the hydrophobic phase. A second solution of xanthan gum, carbopol, and "TWEEN®" 60 (polyoxyethylenesorbitan stearate) is prepared in saline and emulsified with the hydrophobic phase while stirring at 40° C.

Formula D: the formulation contains 12% lecithin, 8% corn starch, and 80% saline. Lecithin is heated to 40° C. and suspended into saline. Corn starch is then added and the mixture is vortexed, heated to 40° C., and sonicated for 5 minutes. The vortexing, heating, and sonicating steps are repeated two more times until a homogeneous semi-solid phase was obtained.

Formula E: the formulation contains 12% lecithin, 3% lanolin, 7% corn starch, and 78% saline. Lanolin and lecithin are heated to 40° C. and suspended in saline containing starch. The mixture is heated, vortexed, and sonicated until a semi-solid phase was obtained.

Formula F: the formulation contains 12% lecithin, 3% polyethylene glycol hydroxy stearate, 7% corn starch, and 78% saline. A mixture of lecithin and polyethylene glycol hydroxy stearate is heated to 40° C. while stirring. Corn starch and saline are then added and mixed thoroughly. The mixture is heated, vortexed, and sonicated to achieve a homogeneous semi-solid formulation.

To add nikkomycin or other chitin synthesis inhibitors to the above formulations of Formulas A-F, nikkomycin is added into each formulation in a vial to achieve a final concentration of about 10% or 100 mg nikkomycin/g formulation. The vial is then heated to about 40° C. followed by vortexing for about 5 minutes. This process is repeated, preferably about 5 times, to achieve complete incorporation of nikkomycin into the formulation.

5.2. PHARMACEUTICALLY ACCEPTABLE VEHICLES

Pharmaceutically acceptable vehicle means a carrier suitable for delivering safe and therapeutically effective amounts of the nikkomycin or other chitin synthesis inhibitor. Such a vehicle includes but is not limited to saline, buffered saline, dextrose, water, glycerol, ethanol, dimethyl sulfoxide, and combinations thereof. The vehicle and nikkomycin or other chitin synthesis inhibitor can be sterile. The vehicle should suit the mode of administration.

In a preferred embodiment, the chitin synthesis inhibitor is formulated in accordance with routine procedures as a pharmaceutical composition adapted for intravenous administration to human beings. Typically, compositions for intravenous administration are solutions in sterile isotonic aqueous buffer. Where necessary, the composition may also include a local anesthetic such as lignocaine or lidocaine to ease pain at the site of the injection. Where the composition is to be administered by infusion, it can be dispensed with an infusion bottle containing sterile pharmaceutical grade water or saline.

5.3. NIKKOMYCINS

In a preferred embodiment of the present invention, the chitin synthesis inhibitor is a nikkomycin. Nikkomycins are a class of chitin synthesis inhibitors that are thought to act by inhibiting the enzyme chitin synthase (Cabib, E., 1991, Antimicrob. Agents Chemother. 35:170-173). Nikkomycins are peptidyl nucleoside antibiotics produced by Streptomyces (Isono et al., 1965, Agricultural Biology and Chemistry 29:848-854).

Figure 1:
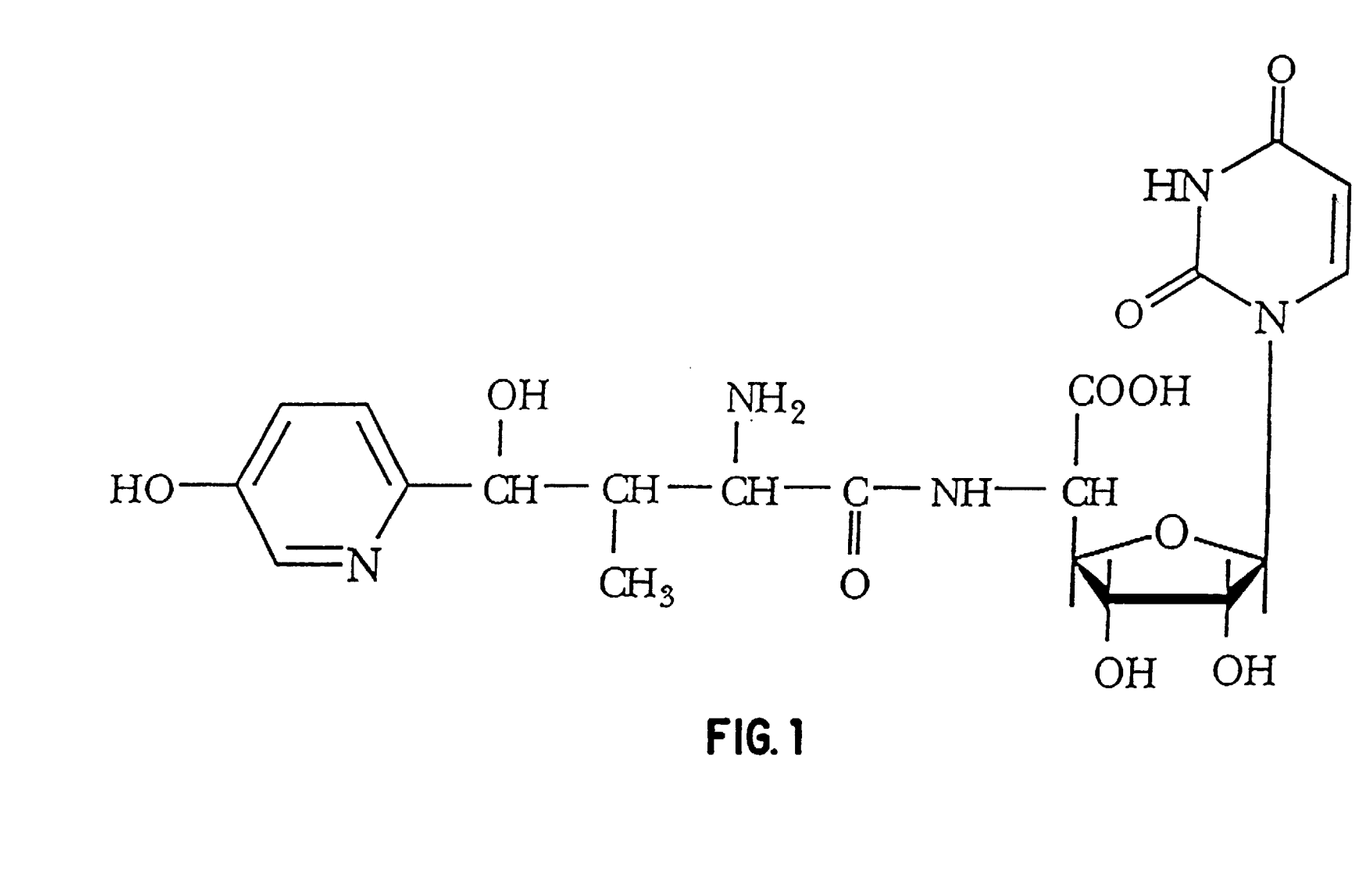
FIG. 1 shows the chemical structure of nikkomycin Z.

One of the better studied nikkomycins is nikkomycin Z. See FIG. 1 for the chemical structure of nikkomycin Z. Due to its close structural resemblance to UDP-N-acetylglucosamine, the substrate of chitin synthase, nikkomycin Z is a potent inhibitor of this enzyme in fungi, insects, and arthropods (the only organisms containing chitin). The available evidence suggests that nikkomycin Z shows no toxicity against plants, fish, or mammals under reasonable doses.

Methods for the purification of nikkomycins are described in U.S. Pat. No. 4,552,954 and U.S. Pat. No. 4,315,922. Also, U.S. Pat. No. 4,552,954 and U.S. Pat. No. 4,315,922 describe various types of nikkomycins, e.g., nikkomycin X, nikkomycin Z, nikkomycin I, nikkomycin J, nikkomycin M, nikkomycin N, nikkomycin D, nikkomycin E. Various nikkomycins are useful in the practice of the present invention. In addition, derivatives of nikkomycins are useful in the methods of the present invention. Additional methods of purifying nikkomycins suitable for use in the present invention are described in Krainer et al., 1987, Anal. Biochem. 160:233-239.

5.4. CALCULATION OF DOSE RATES

In order to attain a desired minimum effective concentration (MEC) of nikkomycin, e.g., nikkomycin Z, (or other chitin synthesis inhibitor) in the plasma of a subject mammal, it is necessary to calculate the proper rate of infusion (for continuous intravenous administration) or rate of release (for sustained release formulations) of nikkomycin, e.g., nikkomycin Z, for the given subject mammal. For ease of discussion, the following is discussed using nikkomycin Z as an illustrative example; as would be understood by one skilled in the art, this discussion applies equally to other chitin synthesis inhibitors useful in the methods of the present invention.

To calculate the proper rates of infusion and release, one must take into account the body weight of the mammal (BW) and the pharmacokinetic parameters of elimination rate ($k_{el}$), volume of distribution ($V_d$), distribution coefficient ($\Delta'$), and elimination half life ($t_{1/2}$) for nikkomycin Z in the mammal. Pharmacokinetic parameters of nikkomycin Z are determined following single i.v. push injection. Blood samples are taken over a period of 4–24 hours and plasma levels of nikkomycin Z are determined using high performance liquid chromatography (HPLC). The nikkomycin Z plasma concentration vs. time is used to calculate the pharmacokinetic parameters of elimination rate ($k_{el}$), volume of distribution ($V_d$), distribution coefficient ($\Delta'$), and elimination half life ($t_{1/2}$). For details as to the calculation of these pharmacokinetic parameters, see *Handbook of Basic Pharmacokinetics*, W. A. Ritschel, 1st edition, Drug Intelligence Publications, Inc., Hamilton, Ill. 60234.

The following equation is then used to determine infusion rate or release rate to keep the plasma concentration of nikkomycin Z above the minimum effective concentration (MEC).

$$R° = MEC \times \Delta' \times BW \times k_{el}$$

where:
$R°$ is the infusion rate or rate of release in µg/hr
MEC is in µg/ml
$\Delta'$ is in units of ml/kg
BW is body weight in kg
$k_{el}$ is in units of hours$^{-1}$
Alternatively, the following equation may be used:

$$R° = V_d \times k_{el} \times C^{ss}_{av}$$

where:
$R°$ is the infusion rate or rate of release in µg/hr
$V_d$ is in units of ml
$k_{el}$ is in units of hours$^{-1}$
$C^{ss}_{av}$ is in units of µg/ml and is equal to the chitin synthesis inhibitor concentration at steady state. Assume this equals or exceeds the MEC.

For human subjects with *Candida albicans* infections and for treatment with nikkomycin Z, the MEC is in the range of 0.5 µg/ml to 500 µg/ml, preferably 5 µg/ml to 300 µg/ml, and most preferably 10 µg/ml to 200 µg/ml. Similar values are useful for treatment with other nikkomycins of *Candida albicans* infections in humans.

For human subjects being treated with nikkomycin Z or other nikkomycins, R° is in the range of about 30 to 1,000 mg/kg/day, preferably 50 to 500 kg/mg/day, and most preferably 100 to 350 mg/kg/day. Other preferred ranges are 30 to 100 mg/kg/day, 30 to 500 mg/kg/day, and 30 to 50 kg/mg/day.

HPLC can be performed according to well known methods in the art, e.g., see Chapman et al., Antimicrob. Agents Chemother., 1992, 36:1909-1914. See also Section 6.4.

The MEC for a particular fungus can be estimated from the concentration that kills or inhibits the growth of that fungus in vitro. For examples of studies of the killing or inhibition of growth of fungi in vitro, see Hector and Schaller, Antimicrob. Agents Chemother., 1992, 36:1284-1289.

Generally, the MEC should be maintained for a period of three to four days and thus the continuous intravenous infusion or other method of continuous delivery should be for a period of at least three to four days. In some cases, monitoring of the course of infection will dictate that treatment should be for a time somewhat less or somewhat greater than this, i.e., those infections that respond quickly will require less time; those that are more refractory will require correspondingly greater time. It is well within the ability of one of ordinary skill in the art to determine the proper time of treatment.

6. EXAMPLES

6.1. YEAST STRAINS AND CONDITIONS OF CULTURE

*Candida albicans* strain B311 (originally obtained from H. Hasenclever, National Institutes of Health, Bethesda, Md.) was employed in the following examples. For growth of yeast inocula, frozen culture aliquots were inoculated into 2% glucose, 1% yeast extract broth and grown at 35° C. with shaking until the culture entered the early log phase of growth. Yeast were collected by centrifugation, washed, and adjusted to the appropriate concentration in sterile phosphate-buffered saline (PBS).

6.2. REDUCTION OF YEAST LOAD IN ORGANS OF INFECTED ANIMALS

A rat model of systemic candidiasis was used to assess the effect of nikkomycin Z in vivo. In two separate experiments, outbred albino rats (strain S/A, Simonsen Laboratories, Gilroy, Calif.), 195–205 g average weight, were infected intravenously with *C. albicans* B311 with inoculum levels of $6.2 \times 10^5$ and $1.2 \times 10^6$ cfu/rat, respectively (cfu=colony forming units). The inoculum and the subsequent drug treatment was administered via an indwelling catheter placed in the jugular vein that was "tunneled" out the back and placed inside a protective, flexible, metal sheath. For both experiments, therapy was initiated 12–14 h after infection with nikkomycin Z (formulated in a vehicle of 2% dimethylsulfoxide (DMSO)/ 98% dextrose (5%)) administered continuously at 330 mg/kg/day; control animals were treated with vehicle. In the first experiment, animals were treated continuously for 72 h. In the second experiment, animals were treated continuously for 96 h. Drug and vehicle were administered continuously at a volume of one ml per hour. At 7 or 9 h after cessation of treatment, respectively, all animals were euthanized for the removal of kidneys, which were cultured for the quantitative recovery of viable yeast. From each animal, the two kidneys were placed into tared, sterile tubes (one tube per animal, i.e., two kidneys per tube) containing ten ml of sterile PBS. The kidneys were then weighed and the tube contents homogenized. Organ homogenates were diluted in serial fashion and cultured on Sabourauds agar plates containing 50 µg/ml chloramphenicol for the quantitative recovery of viable yeast. The plates were incubated overnight at room temperature and colonies enumerated. Calculations were made to determine the $\log_{10}$ cfu's per gram of tissue for each animal.

The results of the quantitative cultures are shown in Table 1. In animals treated for either 72 or 96 h, the effects of continuous administration of nikkomycin Z resulted in a decrease in approximately two $\log^{10}$ units of viable yeast per gram of tissue.

TABLE 1

Effects of nikkomycin Z continuous infusion on cfu/gm kidney

| Group | Geometric mean $\log_{10}$ CFU/gm ± S.E.M. | |
|---|---|---|
| | Exp. 1* | Exp. 2** |
| Vehicle | 5.35 ± .29 | 5.67 ± .31 |
| Nikkomycin Z | 3.09 ± .16 | 3.73 ± .05 |

*330 mg/kg/day nikkomycin Z (or vehicle) given over 72 h period
**330 mg/kg/day nikkomycin Z (or vehicle) given over 96 h period Experiments similar to those described above were performed to determine the effectiveness of low doses of Nikkomycin Z in reducing the yeast load in organs of infected animals in the rat model of systemic candidiasis. Experimental details such as yeast used, growth conditions, rats used, and methods of inoculation and drug delivery were as described above in Sections 6.1 and 6.2. Inoculum levels were $1\times10^6$ cfu/rat. Therapy was initiated 14 h after yeast infection and nikkomycin Z was administered continuously at either 33 or 100 mg/kg/day for a total of 96 h; control animals were treated with vehicle. Test solutions were delivered from syringes using infusion pumps; syringes and solutions were changed daily. After cessation of treatment, all animals were euthanized for the removal of kidneys, which were cultured for the quantitative recovery of viable yeast. Organ removal and culture were done as above. Organ homogenates were cultured on Sabourauds agar and incubated overnight for the enumeration of yeasts as above.

The results are shown in Table 2. In animals treated for 96 h, continuous administration of nikkomycin Z resulted in a decrease in approximately 1 $\log_{10}$ units of viable yeast per gram of tissue with 33 mg/kg/day, and 2 $\log_{10}$ units with the 100 mg/kg/day dose level.

TABLE 2

Effects of nikkomycin Z continuous infusion on cfu/gm kidney

| Group | Dose (mg/kg/day) | Geometric mean $\log_{10}$ CFU/gm ± S.E.M. | p value vs. Control | p value vs. 33 mg/kg |
|---|---|---|---|---|
| Vehicle | — | 5.37 ± 0.14 | — | — |
| Nikkomycin Z | 33 | 4.23 ± 0.15 | 0.004 | — |
| Nikkomycin Z | 100 | 3.48 ± 0.15 | <0.001 | 0.007 |

These results demonstrate that doses of nikkomycin Z as low as 33 mg/kg/day are sufficient to dramatically reduce the yeast load in organs of infected animals and stand in surprising contrast to the prior art in which doses of nikkomycin z comparable or higher than the 33 mg/kg daily dose used above failed to result in any substantial or permanent improvement over that seen with controls.

6.3. PREVENTION OF MORTALITY IN INFECTED ANIMALS

Using methods similar to those described above, rats were infected intravenously with a higher inoculum level; i.e., $3.2\times10^6$ cfu/rat, to induce mortalities. Fourteen hours after infection, treatment by continuous infusion was initiated with nikkomycin Z administered continuously at 330 mg/kg/day; control animals were treated with vehicle. Treatment was continued for 96 h, then animals were held for a total of 28 days for observation of mortalities. The results are shown in FIG. 2.

Figure 2:
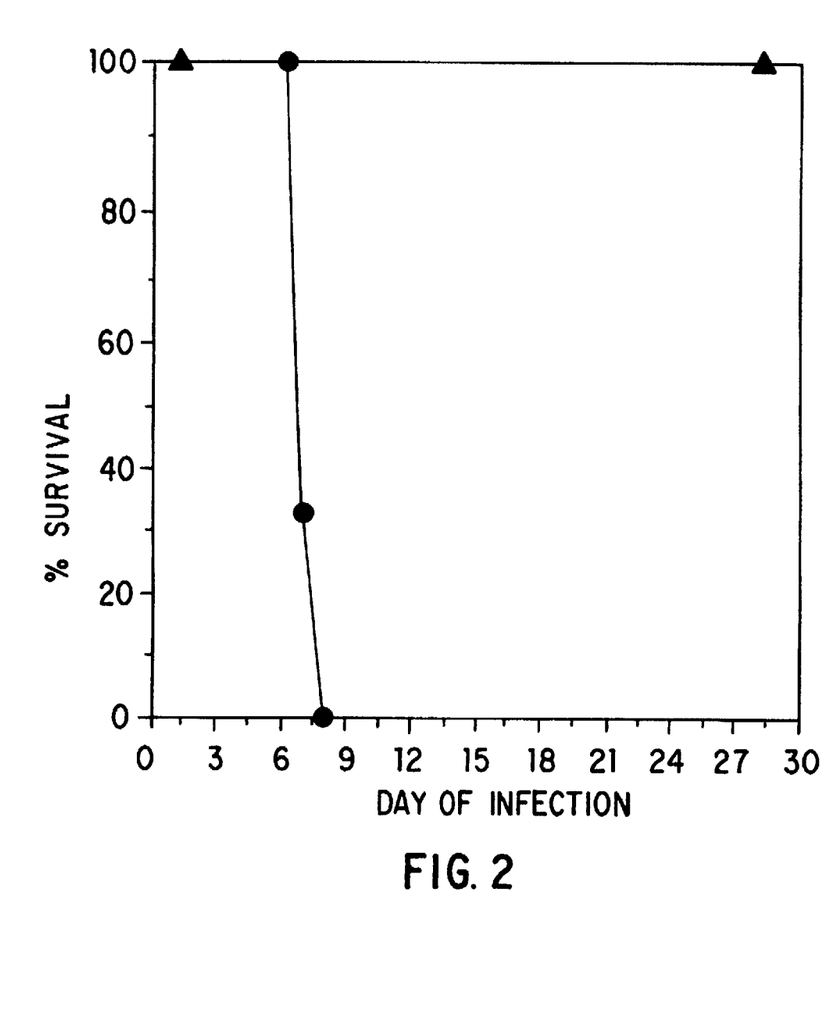
FIG. 2 shows the prevention of mortality by nikkomycin Z in rats infected with otherwise lethal doses of *Candida albicans*. See Section 6.3 for details. —▲—= control rats, no nikkomycin Z treatment; —△—= rats treated with of nikkomycin Z at 330 mg/kg/day.

As shown in FIG. 2, all animals receiving vehicle died by day 8. In contrast, all animals receiving nikkomycin Z by continuous infusion survived the entire observation period. This demonstrates that continuous intravenous infusion with nikkomycin Z is highly effective at preventing mortality in animals with an otherwise fatal infection of *Candida albicans*.

Experiments similar to those described above in this Section were performed to determine the effect of low doses of nikkomycin Z in preventing mortality in animals infected with *Candida albicans*. Using methods similar to those described above, rats were infected intravenously with $1.05\times 10^7$ cfu/rat of *C. albicans* B311, a dose that would normally rapidly induce mortalities. The inoculum and the subsequent drug treatment was administered via an indwelling catheter placed in the jugular vein. For the experiment, therapy was initiated 14 h after infection with yeast and nikkomycin Z was administered continuously at 33 or 100 mg/kg/day; control animals were treated with vehicle. All animals were treated continuously for 96 h, with test solutions delivered from syringes using infusion pumps. Syringes and solutions were changed daily. Animals were held for a total of 30 days for observation of mortalities. The results are shown in FIG. 4.

Figure 4:
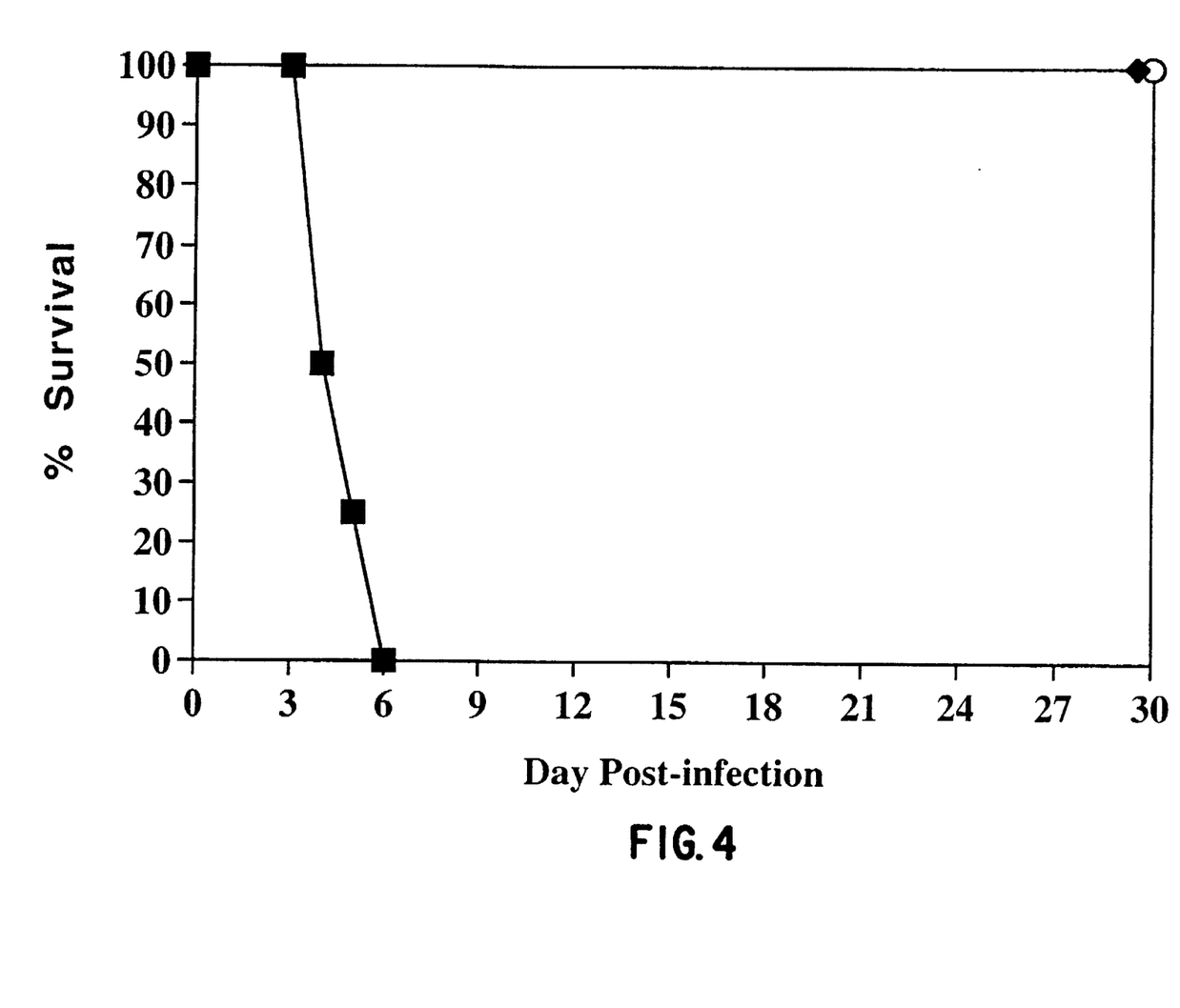
FIG. 4 shows the prevention of mortality by continuous intravenous infusion of 33 or 100 mg/kg/day of nikkomycin Z in rats infected with otherwise lethal doses of *Candida albicans*. See Section 6.3 for details. —■—= control rats, no nikkomycin Z treatment; —♦—= rats treated with nikkomycin Z at 33 mg/kg/day. —○—= rats treated with nikkomycin Z at 100 mg/kg/day.

As shown in FIG. 4, all animals receiving vehicle died by day 6. In contrast, all animals receiving nikkomycin Z at either 33 or 100 mg/kg/day by continuous infusion survived the entire observation period. These results demonstrate that doses of nikkomycin Z as low as 33 mg/kg/day are sufficient to prevent mortality in infected animals and stand in surprising contrast to the prior art in which doses of nikkomycin Z comparable or higher than the 33 mg/kg daily dose used above failed to result in any substantial or permanent improvement over that seen with controls.

6.4. SUSTAINED RELEASE FORMULATIONS OF NIKKOMYCIN Z

A semi-solid sustained release formulation of nikkomycin Z was prepared by blending nikkomycin Z into a gel consisting of 12% (w/w) "PLURONIC®" F127 (copolymers of ethylene oxide and propylene oxide) in water to achieve a final concentration of 180 mg/ml of nikkomycin Z. Six cannulated rats each received 1 ml of this sustained release formulation subcutaneously. This represented a dosage of about 500 mg/kg per rat. Blood samples of 1 ml were withdrawn from each rat at 30 minutes and at 1, 3, 6, 10, 13, 24, 33, and 48 hours. The withdrawn volume was replaced with 2 ml of 5% dextrose. The blood was transferred into a tube containing 0.5 ml of 100 units of heparin in 5% dextrose. The blood was centrifuged at 500 g for 5 minutes and then at 3,000 g for 20 minutes. The recovered plasma, about 1 ml, was frozen until analysis.

For analysis, 1 ml alcohol USP was added to 0.5 ml of each thawed plasma sample. The sample was then vortexed and centrifuged. The resulting supernatant was concentrated via centrifugal evaporation. The samples were reconstituted with 250 ml water and analyzed by HPLC. HPLC was performed on an HP Series 1050 instrument with diode array detector; the column was a Metachem Inertsil C18 column, 4.6×250 mm; the mobile phase was acetonitrile/0.01 M heptane sulfonic acid with 0.2% acetic acid; the gradient was 10% to 50% acetonitrile in 15 minutes; the flow rate was 1 ml per minute; the injection volume was 50 µl; UV absorption was monitored at 260 nm and 280 nm; and the run time was 20 minutes.

Figure 3:
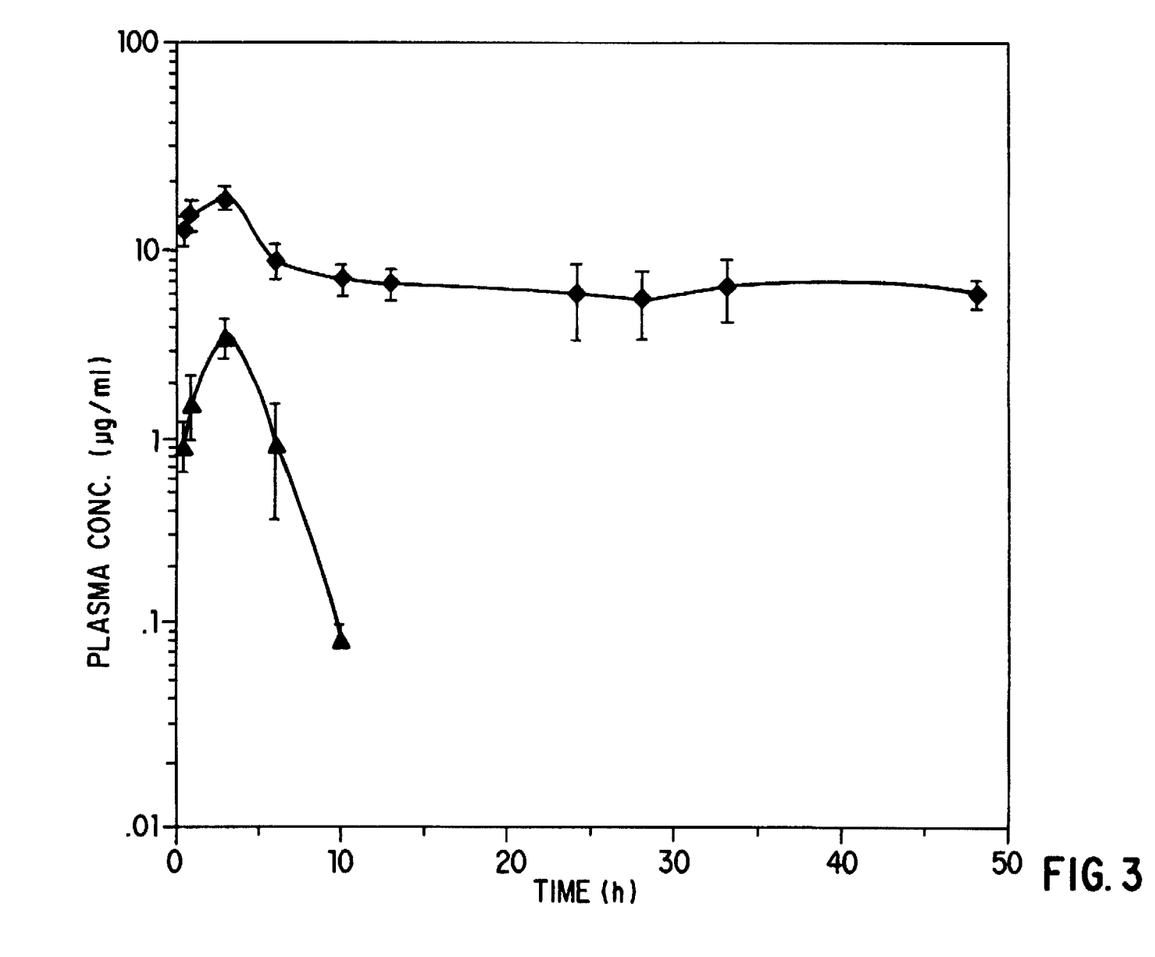
FIG. 3 shows plasma levels of nikkomycin Z and nikkomycin Z related compounds following subcutaneous administration via sustained release formulation of 500 mg/kg of nikkomycin Z in rats. See Section 6.4 for details. —♦—= total nikkomycins, i.e., nikkomycin Z and nikkomycin Z related compounds; —▲—= nikkomycin Z.

The concentrations of the parent compound (nikkomycin Z) and total nikkomycin Z related compounds (parent plus metabolites) were derived from the HPLC analysis and then plotted against time as shown in FIG. 3. As can be seen from FIG. 3, the sustained release gel achieved near steady state plasma concentrations of about 6 µg/ml for the nikkomycin Z total compounds. The mean residence time (MRT) for nikkomycin Z total compounds increased from 0.2 hr (a value obtained when this experiment was carried out using a single intravenous administration) to 16.6 hr for this sustained release formulation.

An additional sustained release formulation was prepared by incorporating nikkomycin Z into Formula A (decribed in Section 5.1 above). Formula A contained 12% lecithin, 5% ethyl alcohol, 5% dimethylsulfoxide (DMSO), 10% corn starch, and 68% saline. To prepare Formula A, lecithin was suspended into a mixture of ethyl alcohol and DMSO using 5 minutes sonication followed by 5 minutes of vortexing. Corn starch was then added along with saline and the mixture was vortexed, heated to 40° C., and sonicated for 5 minutes. The vortexing, heating, and sonicating steps were repeated two more times until a homogeneous semi-solid phase was obtained.

Nikkomycin Z was added to the above Formula A in a vial to achieve a final concentration of 10% or 100 mg nikkomycin Z /g formulation. The vial was then heated to about 40° C. followed by vortexing for ~5 minutes. This process was repeated 5 times to achieve complete incorporation of nikkomycin Z into the formulation.

The ability of Formula A to deliver a minimal effective concentration (MEC) of nikkomycin Z was compared to that of two other methods of delivering nikkomycin Z: (1) continuous intravenous administration in dextrose solution; and (2) a hydroxypropylmethylcellulose (HPMC)-based semi-solid formulation.

The experimental animals were outbred male albino rats (strain S/A, Simonsen Laboratories, Gilroy, Calif.), 350–400 g average weight, housed one per cage, fed rodent chow and water ad libitum, and identified by ear tags. Rats receiving continuous intravenous administration of nikkomycin Z were cannulated in the left carotid artery and right jugular vein. Rats receiving subcutaneous formulations were cannulated in the left carotid artery.

Continuous intravenous administration involved a 2 hour loading dose of 20 mg/kg/hour nikkomycin Z and then an infusion rate of 33 mg/kg/day over 24 hours. The formulation contained 1 mg/ml nikkomycin Z in sterile 5% dextrose. Blood samples of 1 ml were withdrawn at 0, 0.25, 0.5, 1, 2, 4, 6 and 12 h. The withdrawn volume was replaced with 2 ml of 5% dextrose.

The HPMC-based semi-solid formulation consisted of 3% hydroxypropylmethylcellulose (HPMC), 2% "TWEEN®" 20 (polyoxyethylenesorbitan laurate), 5% ethyl alcohol, and 90% saline. HPMC was suspended in saline and vortexed for 5 minutes. The weight of the suspension was determined and the mixture was then heated to 40° C. while stirring for a period of 8 hours until a homogeneous, thick solution was obtained. Upon cooling, the loss in weight due to evaporation was determined and then corrected by the addition of distilled water. Ethyl alcohol and "TWEEN®" 20 were then added and the mixture was stirred for 10 minutes to achieve a homogeneous formulation. Nikkomycin Z was added to the HPMC-based formulation in the same manner as described above for Formula A. Rats receiving either sustained release formulation were given 2 ml of nikkomycin Z sustained release formulation subcutaneously. This represented a dosage of about 570 mg/kg. Blood samples of 1 ml were withdrawn at 0, 0.25, 0.5, 1, 2, 3, 6, 9, and 12 hours. The withdrawn volume was replaced with 2 ml of 5% dextrose.

Blood was transferred into a tube containing 0.5 ml of 100 units of heparin in 5% dextrose. The blood was centrifuged at 500 g for 5 minutes and then at 3,000 g for 20 minutes at 4° C. The recovered plasma, about 1 ml, was frozen until analysis. Plasma samples were thawed in a water bath and 1.0 ml of plasma samples were analyzed using an HPLC/SPE based test method. Nikkomycin Z was extracted from the plasma samples using solid phase extraction (SPE) columns. The SPE matrix was phenylboronate (PBA) which covalently binds nikkomycin Z at high pH. After washing with 20 mM sodium carbonate/bicarbonate alkaline buffer, nikkomycin Z was eluted from the extraction column with a 20 mM glycine solution at pH 1.2. Following a drying and reconstitution step, nikkomycin Z plasma concentration was determined using reverse phase HPLC. The plasma concentrations of nikkomycin Z derived from the HPLC analysis were plotted against time. Then, the plasma concentration vs. time data were subjected to statistical analysis to determine pharmacokinetic parameters.

Figure 5:
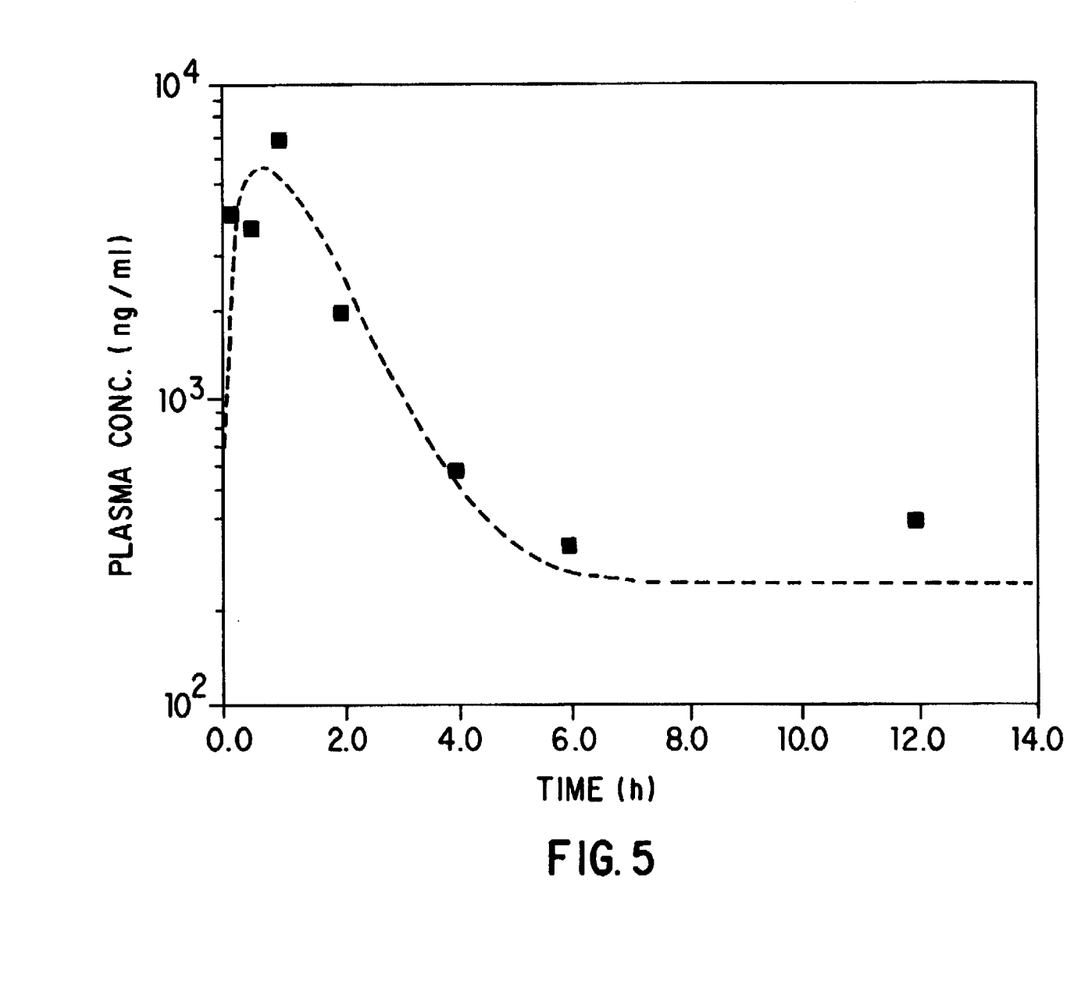
FIG. 5 shows plasma concentration of nikkomycin Z following continuous intravenous administration of nikkomycin Z. A loading dose of 40 mg/kg was infused over a period of 2 hours. A maintenance of dose of 33 mg/kg/day was then infused to achieve a steady state concentration of about 170 ng/ml. See Section 6.4 for details.

Nikkomycin Z plasma concentrations following continuous intravenous administration in dextrose solution using a 2 hour loading dose of 20 mg/kg/h and an infusion rate of 33 mg/kg/day are shown in FIG. 5. As can be seen, plasma concentrations rose following the loading dose to reach a maximum concentration of about 6600 ng/ml at $T_{max}$ of 1 hour. Following the start of the infusion of 33 mg/kg/day, nikkomycin Z concentrations declined rapidly to reached a steady state concentration of about 170 ng/ml.

Figure 6:
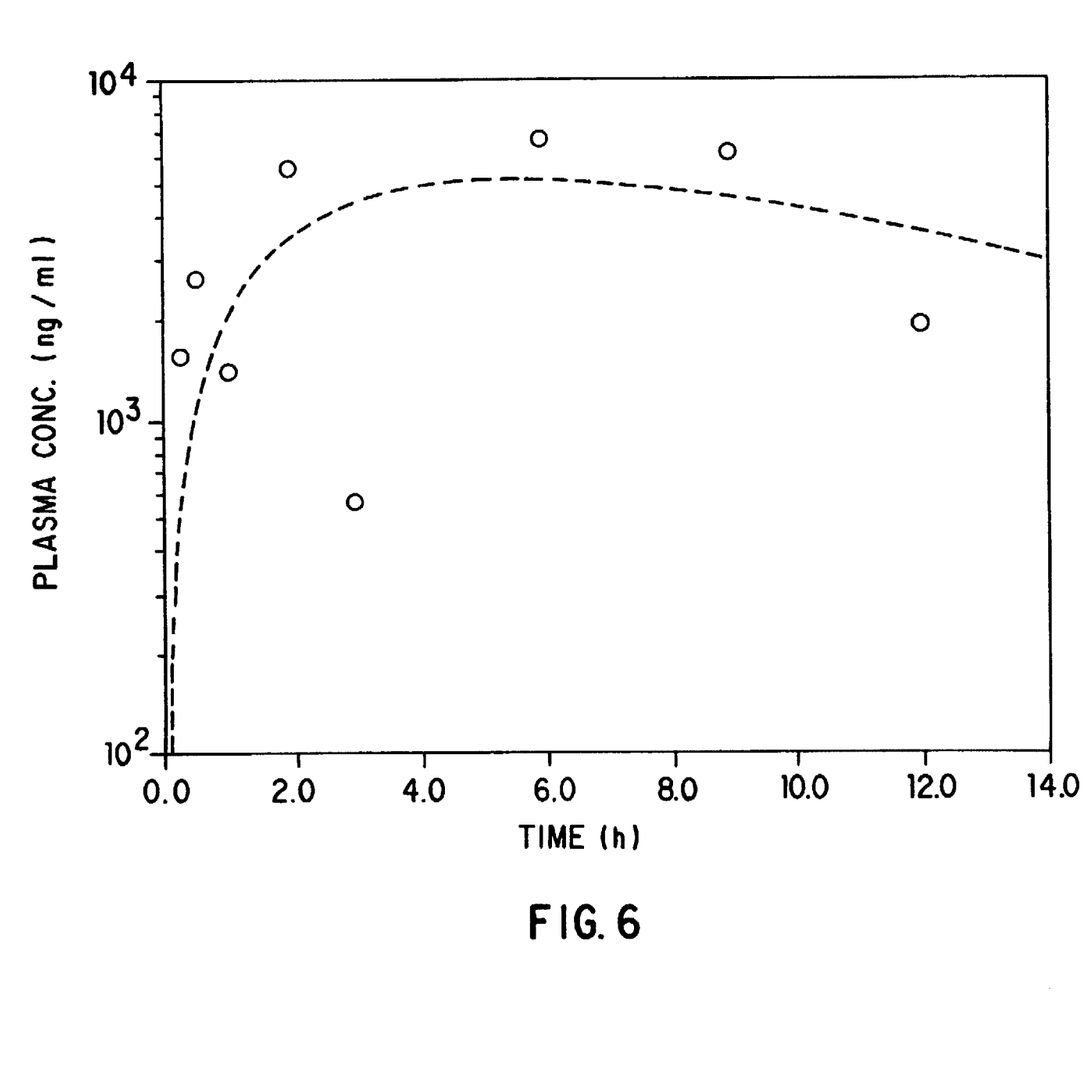
FIG. 6 shows plasma concentration of nikkomycin Z following subcutaneous administration of 570 mg/kg of nikkomycin Z via sustained release formulation Formula A. A near steady state plasma concentration of about 5000 ng/ml was achieved. See Section 6.4 for details.

Plasma concentrations of nikkomycin Z vs. time following subcutaneous injection of nikkomycin Z in Formula A are shown in FIG. 6. As can be seen from FIG. 6, the sustained release semi-solid Formula A achieved near steady state plasma concentrations of about 5000 ng nikkomycin Z/ml. The mean residence time (MRT) of nikkomycin Z was prolonged to about 12 hours compared with 0.2 hours for nikkomycin Z following continuous intravenous administration. Maximum concentration ($C_{max}$) of 5200 ng/ml was reached at a $T_{max}$ of 5.6 hours.

A comparison of the pharmacokinetic parameters obtained with Formula A and the HPMC-based formulation is shown in Table 3.

TABLE 3

The effect of formulations on pharmacokinetic parameters of nikkomycin Z following sub-cutaneous administration in rats.

| Dosage Form | $C_{max}$ (µg/mL) | $t_{max}$ (hr) | AUC (µg hr/mL) | MRT (hr) |
|---|---|---|---|---|
| Formulation A | 5.2 | 5.6 | 82.1 | 11.9 |
| Formulation HPMC | 3.5 | 1.4 | 13.5 | 2.9 |

As can be seen from Table 3, relative bioavailability of nikkomycin Z from the HPMC-based formulation was lower than from Formula A based on a comparison of the areas under the curves (AUCs). Most of the nikkomycin Z was released rapidly from the HPMC-based semi-solid formulation as evidenced by the short $T_{max}$ (only 1.4 hours) and the rapid disappearance of nikkomycin Z from the circulation (represented in the short MRT of only 2.9 hours).

As shown in Sections 6.2 and 6.3 above, continuous intravenous administration of nikkomycin Z at an infusion rate of 33 mg/kg/day for 4 days was able to significantly reduce the yeast organ load and achieve complete protection of rats against a lethal challenge with Candida albicans. Based on the pharmacokinetic infusion study described in this Section, a steady state of nikkomycin Z concentration of about 173 ng/ml is achieved following the infusion of 33 mg nikkomycin Z/day. As the comparative data described immediately above with respect to Formula A and the HPMC-based sustained release formulation show, this plasma concentration (MEC) could also be achieved and sustained using sustained release formulations such as, but not limited to, Formula A as evidenced by results described above.

The present invention is not to be limited in scope by the specific embodiments or specific examples described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of treating a human infected with a fungus which is a Candida spp., comprising administering to the human a chitin synthesis inhibitor selected from Nikkomycin X and Nikkomycin Z in a continuous fashion in sufficient quantity to maintain a minimum effective concentration in the target organ or plasma.

2. The method of claim 1 which the fungus is selected from the group consisting of Candida albicans, Candida parapsilosis, Candida krusei, Candida tropicalis, and Candida glabrata.

3. The method of claim 2 in which the fungus is Candida albicans.

4. The method of claim 1 in which the nikkomycin is nikkomycin Z.

5. The method of claim 1 in which the nikkomycin is nikkomycin X.

6. The method of claim 1 in which the chitin synthesis inhibitor is administered in a continuous intravenous fashion.

7. The method of claim 1 in which the chitin synthesis inhibitor is administered by a sustained release method.

8. The method of claim 7 in which the sustained release method is a per-oral method.

9. The method of claim 8 in which the sustained release method is by subcutaneous implantation.

10. The method of claim 1 in which the human is immunocompromised.

11. The method of claim 1 in which the human is suffering from AIDS.

12. The method of claim 1 in which the fungus is Candida albicans, the chitin synthesis inhibitor is nikkomycin Z administered in a continuous intravenous fashion, and the mammal is a human.

13. The method of claim 1 in which the fungus is Candida albicans, the chitin synthesis inhibitor is nikkomycin Z administered by a sustained release method, and the mammal is a human.

14. The method of claim 1 in which an infusion rate between 30 and 500 mg/kg/day is used.

15. The method of claim 14 in which an infusion rate between 30 and 50 mg/kg/day is used.

16. The method of claim 12 in which an infusion rate between 30 and 500 mg/kg/day is used.

17. The method of claim 16 in which an infusion rate between 30 and 50 mg/kg/day is used.

18. A pharmaceutical composition comprising nikkomycin X or nikkomycin Z in combination with a pharmaceutically acceptable carrier consisting of a sustained release formulation the ingredients of which are selected from lecithin, ethyl alcohol, dimethylsulfoxide, saline, lanolin, cottonseed oil, polyoxyethylene sorbitan monolaurate, polyoxyethylene sorbitan monopalmitate, stearic acid, hydroxymethylcellulose, hydroxypropylmethylcellulose, carboxypolymethylene (carbopol), polyethylene glycol, hydroxy stearate, petrolatum white, sorbitan monopalmitate, mineral oil, polyoxyethylene sorbitan monostearate, beeswax, xanthan gum, and corn starch.

19. A pharmaceutical composition of claim 1 comprising nikkomycin Z in combination with a pharmaceutically acceptable carrier consisting of a sustained release formulation which contains 12% lecithin, 5% ethyl alcohol, 5% dimethylsulfoxide, 10% corn starch, and 68% saline.

20. The composition of claim 18 in which the sustained release formulation contains 3% lanolin, 14% cottonseed oil, 6% polyoxyethylene sorbitan monopalmitate, 4% stearic acid, 2% hydroxymethylcellulose, 1% carbopol, and 70% saline.

21. The composition of claim 18 in which the sustained release formulation contains 2% polyethylene glycol hydroxy stearate, 2% petrolatum white, 2% polyoxyethyene sorbitan monolaurate, 4% sorbitan monopalmitate, 2.5% mineral oil, 3.5% polyoxyethylene sorbitan monostearate, 2% carboxypolymethylene 2% beeswax, 1% xanthan gum, and 79% saline.

22. The composition of claim 18 in which the sustained release formulation contains 12% lecithin, 8% corn starch, and 80% saline.

23. The composition of claim 18 in which the sustained release formulation contains 12% lecithin, 3% lanolin, 7% corn starch, and 78% saline.

24. The method of claim 1 in which the sustained release formulation contains 12% lecithin, 3% polyethylene glycol hydroxy stearate, 7% corn starch, and 78% saline.

25. The composition of claim 1 in which the sustained release formulation contains 3% hydroxypropylmethylcellulose, 2%, polyoxyethylene sorbitan monolaurate 5% ethyl alcohol, and 90% saline.

* * * * *